US008236794B2

(12) United States Patent
Pfirrmann

(10) Patent No.: US 8,236,794 B2
(45) Date of Patent: Aug. 7, 2012

(54) TREATMENT OF MESOTHELIOMA

(75) Inventor: Rolf W. Pfirrmann, Lucerne (CH)

(73) Assignee: Ed. Geistlich Soehne AG fuer Chemische Industrie, Wolhusen (CH)

( * ) Notice: Subject to any disclaimer, the term of this patent is extended or adjusted under 35 U.S.C. 154(b) by 0 days.

(21) Appl. No.: 10/950,670

(22) Filed: Sep. 28, 2004

(65) Prior Publication Data

US 2005/0119254 A1    Jun. 2, 2005

Related U.S. Application Data

(60) Provisional application No. 60/506,491, filed on Sep. 29, 2003.

(51) Int. Cl.
*A61K 31/54*    (2006.01)
(52) U.S. Cl. ............... 514/222.5; 514/885; 514/908
(58) Field of Classification Search ............... 514/222.5, 514/269, 893, 422, 885, 908; 424/54, 246, 424/195, 774
See application file for complete search history.

(56) References Cited

U.S. PATENT DOCUMENTS

| | | | |
|---|---|---|---|
| 4,337,251 A | | 6/1982 | Pfirrmann |
| 5,108,743 A | * | 4/1992 | Brandely et al. ............. 424/85.5 |
| 5,593,665 A | | 1/1997 | Pfirrmann et al. |
| 5,914,314 A | * | 6/1999 | Falk et al. ........................ 514/11 |
| 6,429,224 B1 | * | 8/2002 | Calabresi et al. ............. 514/422 |
| 6,521,616 B2 | | 2/2003 | Calabresi et al. |
| 6,703,413 B2 | * | 3/2004 | Calabresi et al. ............. 514/422 |
| 6,815,441 B2 | * | 11/2004 | Stendel et al. ............. 514/222.5 |
| 6,987,166 B2 | * | 1/2006 | Ward et al. ..................... 530/328 |
| 2002/0183286 A1 | | 12/2002 | Calabresi et al. |
| 2003/0027818 A1 | * | 2/2003 | Redmond et al. .......... 514/223.8 |
| 2003/0100551 A1 | | 5/2003 | Calabresi et al. |

FOREIGN PATENT DOCUMENTS

| | | |
|---|---|---|
| EP | 1 066 830 A2 | 1/2001 |
| JP | 2002363102 A5 | 12/2002 |
| WO | WO 91/13628 A1 | 9/1991 |
| WO | WO 92/00743 A1 | 1/1992 |
| WO | WO 98/52572 A1 | 11/1998 |
| WO | WO 99/06114 A2 | 2/1999 |
| WO | WO 01/39762 A3 | 6/2001 |
| WO | WO 01/39763 A2 | 6/2001 |

OTHER PUBLICATIONS

Astoul et al—Cancer 1998 15;83 (10), 20992104.*
www.allaboutmalignantmesothelioma.com 2003, 2 pages.*
Markman et al., Cancer 58:18-21.*
NCI, www.cancer.gov, 2000, 2pages.*
Monnet et al. Chest, 121: 1921-1927 (2002).*
Butchart Oncology (1999) 488-500.*
Sterman et al. Chest (1999); 116:504-520.*
Lerza et al. Annals of Oncology 8:385-391 (1997).*
Esposito et al., "Pharmacokinetic Evaluation of Intrapleural Carboplatin in Patients with Malignant Pleural Effusion" Drug Invest. 8(6):352-360, 2004.
Shoji et al., "Phase II Study of Repeated Intrapleural Chemotherapy Using Implantable Access System for Management of Malignant Pleural Effusion" Chest 121(3):821-824, 2002.
Mesothelioma—Medical Definition, http://www.yourdictionary.com/medical/mesothelioma, 1 page, 2009.
Definition of mesothelioma—NCI Dictionary of Cancer Terms, http://www.cancergov/dictionary/?CdrID=44323, 1 page, 2010.
Mesothelioma: on Medical Dictionary Online, http://www.online-medical-dictrionary.org/Mesothelioma.asp?q=Mesothelioma, 1 page, 1988.
Mesothelioma—Medical Dictionary Definition, http://www.medilexicon.com/medicaldictionary.php?t=54517, 1 page, 2006.
Mesothelioma definition—Cancer Information (Cancers, Symptoms, Treatment) on MedicineNet.com, http://www.medterms.com/script/main/art.asp?articlekey=12066, 1 page, 1999.
Stedman's Medical Dictionary 26th Edition, 3 pages, Lippincott Williams & Wilkins, Baltimore, 1995.
Mesothelioma (malignant): MedlinePlus Medical Encyclopedia, http://www.nlm.nih.gov/medlineplus/ency/article/000115.htm, 3 pages, 2009.
Mesothelioma—MayoClinic.com, http://www.mayoclinic.com/health/mesothelioma/DS00779, 3 pages, 2008.
Mesothelioma—Wikipedia, the free encyclopedia, http://en.wikipedia.org/wiki/Mesothelioma, 13 pages, 2010.
Lung cancer—Wikipedia, the free encyclopedia, http://en.wikipedia.org/wiki/Lung_cancer, 21 pages, 2010.
Mesothelioma—definition of mesothelioma in the Medical dictionary—by the Free Online Medical Dictionary, http://medical-dictionary.thefreedictionary.com/mesothelioma, 7 pages, 2010.
Lung cancer—definition of lung cancer in the Medical dictionary—by the Free Online Medical Dictionary, http://medical-dictionary.thefreedictionary.com/lung+cancer, 4 pages, 2010.
Types of lung cancer : Cancer Research UK : CancerHelp UK, http://www.cancerhelp.org.uk/type/lung-cancer/about/types-of-lung-cancer, 6 pages, 2009.
Lung Cancer Types—Mayo Clinic, http://www.mayoclinic.org/lung-cancer/types.html, 1 page, 2001.
Lung Cancer : on Medical Dictionary Online, http://www.online-medical-dictionary.org/Lung+Cancer.asp?q=Lung+Cancer, 1 page, 2010.
Pleura—definition of pleura in the Medical dictionary—by the Free Online Medical Dictionary, Thesaurus, http://medical-dictionary.thefreedictionary.com/pleura, 3 pages, 2007.
Pleura—Definition of pleura at YourDictionary.com, http://www.yourdictionary.com/pleura, 1 page, 2009.
NICI et al. "The effect of taurolidine on human malignant mesothelioma" Proceedings of the American Association for Cancer Research Annual Meeting, 42:189, 2001.

(Continued)

*Primary Examiner* — Brandon Fetterolf
*Assistant Examiner* — Shirley V Gembeh
(74) *Attorney, Agent, or Firm* — Rothwell, Figg, Ernst & Manbeck, P.C.

(57) ABSTRACT

A method of treating mesothelioma in a mammal, whereby a methylol-containing compound is administered to the mammal intrapleurally.

20 Claims, No Drawings

OTHER PUBLICATIONS

Ishizuka et al. "A Case of Successful Intrapleural Nedaplatin Administration for Malignant Pleural Effusion" 39 (4):329-334, 2002.

Kitahara et al. "A Case of Malignant Peritoneal Mesothelioma and Review of the Literature in Japan" 54 (6):1659-1663, 1993.

NICI, Linda, et al. "The effect of taurolidine on human malignant mesothelioma", Database Biosis Biosciences Information Service, Mar. 2001.

Zetter, B., "Angiogenesis and Tumor Metastasis", *Annu. Rev. Med.*, 49:407-24, 1998.

Dimmock, Jr, et al., "Mannich bases of phenolic azobenzenes possessing cytotoxic activity", *Eur. J. Med Chem.* 32:583-594, 1997.

Monson, J.R.T., "Abrogation of tumor necrosis factor (TNF) toxicity in the murine model by taurolidine: support for synergism of TNF with endotoxin", *Br. J. Surg.*, 77(6), Jun. 1990.

Bedrosian, I., et al., "Taurolidine, an analogue of the amino acid taurine, suppresses interleukin 1 and tumor necrosis factor synthesis in human peripheral blood mononuclear cells", *Cytokine*, 3(6):568-575, Nov. 1991.

Monson, J.R.T., "Taurolidine inhibits tumour necrosis factor (TNF) toxicity—new evidence of TNF and endotoxin synergy", *Eur. J. Surg. Onc.* 19:226-231, 1993.

McCourt, M., et al., "Taurolidine inhibits tumor cell growth in vitro and in vivo", *Annals of Surgical Oncology*, 7(9):685-691, 2000.

Monson, J.R.T., "Malignant melanoma: a plague of our times", *Br. J. Surg.*, (76) 997-998, Oct. 1989.

Borman, S., "$A_3$ Receptors: Compounds that activate or inhibit adenosine $A_3$ receptors are being studied for potential therapeutic use in heart disease and cancer", *C&EN*, 37-40, Feb. 2001.

Monson, J.R.T., "Preliminary evidence that taurolidine is antineoplastic as well as anti-endotoxin and anti-microbial", *Br. J. Surg.*, 77(6) Jun. 1990.

Monson, J.R.T., "Taurolidine as an anti-neoplastic agent: a previously undiscovered role?", *Br. J. Surg.*, 77(12) Dec. 1990.

Jacobi, C.A., et al., "New therapeutic strategies to avoid intra- and extraperitoneal metastases during laparoscopy: results of a tumor model in the rat", *Dig. Surg.* 16:393-399, 1999.

Jacobi, C.A., et al., "Influence of different gases and intraperitoneal instillation of antiadherent or cytotoxic agents on peritoneal tumor cell growth and implantation with laparoscopic surgery in a rat model", *Surg. Endosc.* 13:1021-1025, 1999.

Jacobi, C.A., et al., "Inhibition of peritoneal tumor cell growth and implantation in laparoscopic surgery in a rat model", *Amer. J. of Surg.* 174:359-363.

Jacobi, C.A., et al., "Peritoneale instillation von Taurolidin und Heparin zur Verhinderung von intraperitonealem tumorwachstum und trokarmetastasen bei laparoskopischen operationen im rattenmodell", *Langenecks Arch. Chir.* 382:S31-S36, 1997.

\* cited by examiner

TREATMENT OF MESOTHELIOMA

CROSS-REFERENCE TO RELATED APPLICATION

This application claims the benefit of U.S. Provisional Application Ser. No. 60/506,491, filed Sep. 29, 2003.

BACKGROUND OF THE INVENTION

1. Field of the Invention

The present invention relates to the treatment of mesothelioma.

2. Description of the Background Art

Taurolidine (Bis-(1,1-dioxoperhydro-1,2,4-thiadiazinyl-4)methane) was developed by Geistlich Pharma. It is a white crystalline substance, water soluble up to 2%. It is made up of two molecules of taurinamid and three molecules formaldehyde forming a two-ringed structure bridged by a methylene group.

Taurolidine has primarily an antibiotic and anti-endotoxin effect. This effect of taurolidine is mediated by its active metabolites, which are donators of active methylol-groups: Methylol-Taurultam and Methylol-Taurinamide. The active methylol groups inactivate by reacting with the cell wall of bacteria and with the primary amino groups of endotoxins.

Methylol transfer agents, such as the antibacterial and antitoxin drug taurolidine and the related product taurultam, have been shown to exert a modifying effect on the toxicity of tumor necrosis factor (TNF) which is used, inter alia, in the treatment of tumors. Furthermore, the action of methylol transfer agents has been shown to be selective in that the growth of normal cell-lines was not significantly inhibited.

Taurolidine acts by transferring three methylol groups at the site of action, taurultam being an intermediate metabolite which itself transfers a single methylol group with liberation of the very well tolerated compound taurinamide. Thus, the two compounds act by essentially the same mechanism. It should be noted that methylol transfer is to be contrasted with methyl transfer which is characteristic of many highly toxic anti-tumor drugs. Taurolidine and taurultam have low toxicity and are not cytotoxic against normal cells.

In an approach to increase effectiveness of chemotherapy by increasing the concentration of the agent within the tumor and the duration of exposure, chemotherapeutic agents are administered locally relying on diffusion for their distribution. In local therapy, the antineoplastic agent is introduced into the tumor itself or the area around the tumor. The resulting pressure gradient leads to diffusion of the antineoplastic agent into the tumor. This mode of administration not only increases the concentration of the agent within the tumor but also results in much lower concentrations in other tissues compared to systemic administration.

One such approach of local tumor treatment is so-called convection-enhanced drug delivery (CEED) in which the drug is infused into the tumor or the surrounding tissue. The drug is distributed by convective transport, a mode of administration which requires placement of a catheter in most cases. Furthermore, taurolidine solutions have been used as instillation or rinsing solutions of the abdominal cavity in cases of peritonitis. In post-operative instillations, conscious patients have reported as a side-effect irritation and sometimes burning sensations.

Malignant pleural mesothelioma is an uncommon tumor that causes about 1500 deaths per year in the US. However, although it is uncommon, it has been in recent years recorded with increasing frequency. It has gained considerable attention in the press from its association with the environmental carcinogen, asbestos. Mesothelioma associated with exposure to asbestos manifests itself only after a long latency period—from the time of initial exposure to 20 to 40 years or more. Due to considerable exposure to asbestos years ago, it is anticipated that mesothelioma will be a significant health problem for decades to come.

Currently, in Germany for example, 900 new cases of this illness are to be expected each year. Because of the connection of the disease with the use of asbestos-contaminated labor materials and the very long latency stage, it is an exponential increase of new cases is expected.

Therapeutic options extend from watchful waiting to palliative or radical multimodal therapeutic concepts.

SUMMARY OF THE INVENTION

The present invention provides a method of treating mesothelioma in a mammal, comprising administering to said mammal a mesothelioma tumor cell-inhibiting amount of a tumor-inhibiting methylol-containing compound, wherein the methylol-containing compound is administered intrapleurally to said mammal.

DETAILED DESCRIPTION OF THE INVENTION

Mesothelioma is a most difficult disease to treat because surgery, radiotherapy, chemotherapy alone or in various combinations have not had a significant impact on survival in clinical tests (median survival time is 9 to 15 months).

In accordance with one embodiment of the present invention, a method of treating mesothelioma is provided, whereby a patient diagnosed with mesothelioma is administered an amount of a methylol-containing compound sufficient for tumor cell inhibition. In particular mesothelioma of pleural origin is treated with the method of the present invention.

One embodiment comprises administration of a methylol transfer agent in one or more treatment cycles. Each treatment cycle comprising one or more dosing cycles and one or more observations cycles. Further, each dosing cycle comprising an administration phase and a non-administration (rest) phase. The administration phase of each dosing cycle comprising intrapleural adminstration of a daily dose of the methylol transfer agent for about 1 to 8 days into the pleural cavity, followed by a non-administration (rest) phase of about 1 to 14 days during which no methylol transfer agent is administered.

In another embodiment, mesothelioma is treated by intravenous infusion of solutions containing a methylol transfer agent in addition to direct pleural administration as described above.

Preferred methylol transfer agents for treatment of mesothelioma according to the present invention are taurolidine, taurultam, and mixtures thereof.

The present invention relates to the ability of methylol transfer agents, such as taurolidine, to induce cell toxicity, and to enhance Fas-ligand mediated apoptosis. Both taurolidine and its congener taurultam enhance the apoptotic effect of Fas-ligand in cancer cells at drug concentrations which per se show practically no effect on cell viability. For example, in the human malignant glioma cell line LN-229 cell viability was reduced directly following incubation with taurolidine or taurultam alone. This effect enhanced the destruction of LN-229 cells by Fas-ligand. Thus, the use of methylol transfer agents to induce apoptotic cell death provides a means for treating mesothelioma as in the present invention.

The treatment is carried out by administering to a mammal suffering from mesothelioma, compositions containing an active methylol-containing compound, at a dose sufficient to induce death of neoplastic cells by apoptosis. By "methylol-containing compound," or "methylol transfer agent," is meant a compound which contains or is capable of producing a methylol molecule under physiological conditions. A methylol-containing compound is characterized as having a R—CH2—OH group in which R is an alkyl, aryl or hetero group. The invention also includes the use of compounds capable of producing or being converted into a compound containing a R—CH2—OH structure.

Methylol transfer agents include methylol-containing compounds such as taurolidine and taurultam, and their derivatives. The compounds taurolidine and taurultam are disclosed in U.S. Pat. No. 5,210,083. Other suitable methylol-containing compounds include taurinamide derivatives and urea derivatives. Examples of derivatives of taurolidine, taurultam, taurinamide and urea useful in the present invention can be found in WO 01/39763A2. Particularly preferred methylol transfer agents for utilization in accordance with the present invention are taurolidine, taurultam, biologically active derivatives thereof and mixtures thereof.

Alternatively, the compound is a taurinamide derivative, or a urea derivative. Examples of derivatives of taurolidine, taurultam, taurinamide and urea useful in the present invention can be found in WO 01/39763A2.

Other methylol-containing compounds suitable for inducing apoptotic death of cancer cells include but are not limited to 1,3,-dimethylol-5,5-dimethylhydantoin, hexamethylene tetramine, or noxythiolin. By derivative of taurolidine or taurultam is meant a sulfonamide compound which possesses at least 10% of the neoplastic activity of taurolidine or taurultam, respectively. A sulfonamide compound is one having a R2N—SO2R' formula. Derivatives of the compounds described herein may differ structurally from a reference compound, e.g., taurolidine or taurultam, but preferably retain at least 50% of the biological activity, e.g., induction of apoptotic cell death, of the reference compound. Preferably, a derivative has at least 75%, 85%, 95%, 99% or 100% of the biological activity of the reference compound. In some cases, the biological activity of the derivative may exceed the level of activity of the reference compound. Derivatives may also possess characteristics or activities not possessed by the reference compound. For example, a derivative may have reduced toxicity or a prolonged clinical half-life.

Treatment of a mammal suffering from mesothelioma, is carried out by administering to a mammal, e.g., a human patient, a methylol-containing compound. The compound is administered directly to the site of the tumor, e.g., by instillation into the pleural cavity. Alternatively, an erodible or resorbable solid matrix such as a wafer or sponge can be implanted directly into pleural cavity to provide direct administration of the compound. In addition, the methylol-containing compound may be administered systemically, e.g., orally or intravenously to the patient in combination with the intrapleural administration of such methylol-containing compound. Furthermore, a patient may be warmed, e.g., to 42° C. during the period of administration of the methylol-containing compound, for added effect. In accordance with one embodiment, Taurolin® 2% taurolidine is so administered intrapleurally into the pleural cavity by catheter to patients with malignant mesothelioma.

In a preferred embodiment of the invention the therapy with taurolidine for mesothelioma comprises administering taurolidine to a patient diagnosed with mesothelioma in three treatment cycles. In each six week treatment cycle Taurolin® (2% Taurolidine) is administered intrapleurally to the patient. The six week treatment cycle comprising three weeks of Taurolidine treatment (three dosing cycles) and three weeks of observations.

In accordance with another embodiment, Taurolin® 2% taurolidine (taurolidine) is administered both intrapleurally and intravenously to patients with malignant pleural mesothelioma. In a preferred embodiment Taurolidine is administered intravenously either simultaneously with or subsequent to intrapleural administration of Taurolidine in three treatment cycles. In each six week treatment cycle Taurolin® (2% Taurolidine) is administered to the patient, whereby each six week treatment cycle comprises three weeks of Taurolidine treatment (three dosing cycles) and three weeks of observations.

Further, in preferred embodiments, electrolytes are co-administered with the methylol-containing compound. For intrapleural administration of the methylol-containing compound into the pleural cavity, isotonic solutions or infusions of electrolytes may be used. The electrolytes used are pre-warmed to 37-38° C. (body temperature of the patient) prior to administration thereof to the patient. Furthermore, intravenous administration of the methylol-containing compound may be through a slow drop infusion via a central catheter or Port. In a preferred intravenous infusion the slow drop rate is 40 drops per minute. Additionally, intravenous administrations may be supplemented with infusions of complete electrolyte-solutions.

It is particularly beneficial to use taurolidine and/or taurultam, at concentrations sufficient to induce apoptosis in cancer cells, to prevent the spread of metastases, especially following surgical removal of tumors. The mammalian subjects are typically humans. Male or female patients, 18 years of age or older, with histological confirmation of a diagnosis of malignant pleural mesothelioma for which there are no standard therapeutic options available, may be effectively treated. In particular, the treatment of mesothelioma according to the invention includes the use of taurolidine and/or taurultam, at concentrations sufficient to induce apoptosis in cancer cells, for the treatment of such tumors in mammalian subjects.

The treatment of mesothelioma according to the invention includes the use of taurolidine and/or taurultam, at concentrations sufficient to induce apoptosis in cancer cells, for the preparation of pharmaceutical compositions for the treatment of mesothelioma in mammalian subjects by induction of apoptosis. Effective dosage amounts of a methylol transfer agent in accordance with the present invention may comprise pharmaceutical dosage units within the range of about 0.1-1,000 mg/kg body weight, preferably 150-450 mg/kg body weight per day, and most preferably 300-450 mg/kg body weight per day. Alternatively, the dosages can be administered on a grams/day basis, from about 2-60 g/day. Preferred doses may be in the range of about 2.5-30 g/day taurolidine, 4-60 g/day taurultam, or a mixture thereof. Most preferred doses are in the range of about 10-20 g/day taurolidine, 20-40 g/day taurultam, or a mixture thereof.

Suitable formulations for injection or infusion may comprise an isotonic solution containing one or more solubilizing agents, e.g., polyols such as glucose, in order to provide solutions of increased taurolidine or taurultam concentration. Such solutions are described in EP 253662B1. The concentration of taurolidine or taurultam in such solutions may be in the range 1-60 g/liter.

Methylol transfer agents are generally poorly soluble in water. Thus, it is often required to administer relatively large volumes of aqueous solutions containing taurolidine or taurultam, for example 5 g to 30 g of taurolidine and/or taurultam. Preferred solutions for administration in accordance with the present invention contain from about 0.5-3% taurolidine and/or taurultam.

Administration, preferably by instillation, of the total daily dose intrapleurally can be carried out via a catheter in the pleural cavity. Further, in case of a combination of intrapleural and intravenous delivery of the methylol-containing compound, intravenous administration can be carried out at a consistent rate over 24 hours. Intravenous administration may also be via a more rapid infusion schedule of the dose in portions, with breaks between each portion of the dose, e.g. infusion of 250 ml of a 2% taurolidine solution (5 g dose) over 2 hours, followed by a brief break of 4 hours, repeated over the course of a 24 hour infusion period to achieve a total daily dose of 20 g. Alternatively, 250 ml of a 2% taurolidine solution may be infused over one hour, with a one hour break between dose portions, and repeated until the daily dose is achieved, such that the total daily intravenous dose is provided over the course of less than 24 hours (i.e., approximately half the day), with no infusion occurring during the remainder of the day.

In accordance with one embodiment, one bottle (250 ml) of 2% taurolidine is administered intrapleurally in a 24 hour period together with the administration of four bottles (250 ml each) of 2% taurolidine solution intravenously at a rate of 40 drops per minute, one bottle every six hours, to patients with pleural mesothelioma. The dosing cycle generally is an administration phase of daily infusions for five days, followed by a rest phase of two days. Total dosing in a dosing cycle may comprise 25 g taurolidine administered intrapleurally and 100 g taurolidine administered intravenously in each one week cycle.

Alternatively, in accordance with a second embodiment of the invention, the administration phase comprises a daily regimen whereby 250 ml of taurolidine 2% solution is administered intrapleurally and whereby 250 ml of 2% taurolidine solution is administered intravenously over the course of 2 hours, followed by a four hour break, repeated over 24 hours, to achieve the total daily dose.

In accordance with a third embodiment of the invention, the administration phase comprises a daily regimen whereby 250 ml of 2% taurolidine solution is administered intrapleurally and whereby 250 ml of 2% tuarolidine solution is infused over one hour, followed by a one-hour break, and repeated until the daily intravenous dose is achieved. If the total intravenous dose is 20 g (for example), this regimen would provide the daily intravenous dose with four 250 ml infusions of 2% taurolidine over a 7 hour time span. No intravenous infusion occurs for the remainder of the day.

In particularly preferred embodiments, patients are subjected to dosing cycles having an administration phase of at least one day, preferably at least about 3 days, most preferably about 5 days, and up to about 8 continuous days, each administration phase being followed by a non-administration phase of about 1 day to 14 days, during which the methylol-containing compound is not administered to the patient. During each administration phase, the methylol-containing compound is administered each day. For example, administration phases of 1, 2, 3, 4, 5, 6, 7 and/or 8 days can be utilized, and non-administration phases of 1, 2, 3, 4, 5, 6, 7, 8, 9, 10, 11, 12, 13, and/or 14 days may be utilized. At least one dosing cycle is utilized, preferably 3 or more dosing cycles are utilized per treatment cycle. For example, 1, 2, 3, 4, 5, 6, 7, 8, 9, 10 or more sequential dosing cycles can be utilized. At least one treatment cycle, comprising one or more dosing cycles and one or more observation cycles, are utilized, preferably 3 or more treatment cycles can be utilized. An observation cycle comprises a non-administration phase of one or more weeks, preferably three weeks, wherein the patient is observed for safety and response to treatment. Such a regimen has shown surprising and unexpected results with patients. In one particularly preferred embodiment, 3 treatment cycles, each with three dosing cycles and one three week observation cycle are utilized, each dosing cycle comprising an administration phase of 5 days followed by a non-administration phase of 2 days. Preferably, during each day of administration, 250 ml of taurolidine 2% solution is administered intrapleurally to the patient daily and 250 ml of 2% taurolidine solution is intravenously administered to the patient 4 times daily. Such a regimen has surprisingly and unexpectedly resulted in a marked improvement in a patient's condition who suffers from pleural mesothelioma.

In a further embodiment, concomitant administration of anti-convulsants and/or anti-oedema therapy and/or antibiotics and/or fluid and electrolyte replacement is carried out.

1. Anti-Convulsants

Preferably, the patient should be stabilized on anti-convulsive medications prior to treatment, to avoid complications during the treatment. This can conveniently be administered in part on an out-patient basis, as well as to prevent any emergency stabilization on an undesired medication. Valproinic acid is the agent of first choice; the dose should be determined in accordance with blood level checks and administered in 2 single doses. Normally, a dose of 1200 mg to 1500 mg is required. If a treatment with valproinic acid is not sufficient, a combination treatment with lamotrigin is possible. In case of allergies or if valproinic acid is not tolerated, the primary stabilization is to be done with lamotrigin. Phenyloin and carbamazepin are contra-indicated.

2. Anti-Oedema Therapy

An anti-oedema therapy may also be administered, but only if absolutely necessary, because otherwise focal neurological symptoms may occur or become intensified, or intracerebral pressure may symptoms develop. Dexamethason should be given before or after the taurolidine was administered. The anti-oedema therapy should be administered with dexamethason, using the lowest possible dose. To protect the stomach a concomitant therapy with ranitidine 1×150 mg/day may be given. If stomach problems are observed with this therapy, an alternative treatment with antra 1-2×20 mg/day should be administered.

In cases of massively elevated intracerebral pressure and insufficient effectiveness of dexamethason, a therapy with mannitol, in particular at a dosage of up to 4×250 ml/day, is possible.

3. Antibiotic Therapy

A calculated antibiotic treatment with one of the subsequently listed antibiotics may be given, until the arrival of the sensitivity test.

Urinary tract infection:
    primary: Cotrimoxazol
    alternative: Doxycyclin
Pneumonia:
    primary: Erythromycin
    alternative: Doxycyclin The following antibiotics should only be used if absolutely necessary (in the most severe, life-threatening infections) and if the sensitivity situation warrants it: Chino lone, penicillin, cephalosporin 4. Fluid and Electrolyte Replacement in Connection with Intrapleural and Intravenous Taurolidine 2% Therapy An amount of 250 ml of full electrolyte solution is preferably be given at the same time and with the same infusion speed parallel to the infusion with 250 ml taurolidine 2%.

Electrolytes and blood count should be monitored twice per day, and the central vein pressure should be checked once daily.

If a hypernatraemia is observed, first, it should be determined whether dehydration is the cause. Diuretic agents should only be used if fluid is replaced at the same time and after dehydration was ruled out as the reason.

The methylol-containing compound is administered alone or in combination with one or more additional antineoplastic agents. In one embodiment, the supplemental agent kills tumors cells by a mechanism other than apoptosis. For example, an antimetabolite, a purine or pyrimidine analogue, an alkylating agent, crosslinking agent (e.g., a platinum compound), and intercalating agent, and/or an antibiotic is administered in a combination therapy regimen. The supplemental drug is given before, after, or simultaneously with the methylol-containing agent. For example, the methylol transfer agent can be co-administered with a fluoro-pyrimidine, such as 5-fluoro-uracil (5-FU). Effective daily dosage amounts of a fluoro-pyrimidine may be in the range of about 0.1-1,000 mg per pharmaceutical dosage unit. Effective dosage amounts of 5-FU also may be in the range of about 100-5,000 mg/m2 body surface area, preferably about 200-1,000 mg/m2 body surface area, more preferably about 500-600 mg/m2 body surface area. 5-FU typically is provided in 250 mg or 500 mg ampules for injection, or 250 mg capsules for oral administration.

According to another embodiment, a solution containing taurolidine and/or taurultam further contains taurin, in an amount within a range of about 1-20 g/l, preferably about 5 g/l.

Solutions and treatments which may be used in the present invention are set forth in the Examples.

EXAMPLE 1

Isotonic Solution 2% Taurolidine

One suitable composition for direct intrapleuaral administration or intravenous drop infusion is shown below.
Isotonic sterile solution, 100 ml:
2.0 g Taurolidine
5.0 g PVP 16 PF UP aqua dest. ad solut. 100 ml. PH 7.2-7.3
Sterile-filtered and steam sterilization.

EXAMPLE 2

Isotonic Taurolin7 Solution 2% Taurolidine with Taurin and Electrolytes

Another suitable composition for direct intrapleuaral administration or intravenous drop infusion is shown below.
Isotonic sterile solution, 100 ml:
2.0 g Taurolidine
5.0 g PVP 17 PF UP
0.5 g Taurin
0.3 g Sodium chloride
Sterile-filtered and steam sterilization

EXAMPLE 3

Isotonic Taurolin7 Ringer Solution 2% Taurolidine with Taurin and Electrolytes

Another suitable composition for direct intrapleuaral administration or intravenous drop infusion is shown below.
Isotonic sterile solution, 100 ml:
2.0 g Taurolidine
5.0 g PVP 17 PF UP
0.5 g Taurin
0.26 g Sodium chloride
0.0033 g Potassium chloride
0.004 g Calcium chloride 2H$_2$O
0.003 g Sodium hydrogen carbonate
Sterile-filtered and steam sterilization

EXAMPLE 4

Taurolin7 Ringer-Lactate 2% Taurolidine with Taurin and Electrolytes

Another suitable composition for direct intrapleuaral administration or intravenous drop infusion is shown below.
Isotonic sterile solution, 100 ml:
2.0 g Taurolidine
5.0 g PVP 17 PF UP
0.5 g Taurin
0.20 g Sodium chloride
0.013 g Potassium chloride
0.009 g Calcium chloride 2H$_2$O
0.0033 g Sodium lactate 50% solution (Pharmacopeia Europea)
Sterile-filtered and steam sterilization

EXAMPLE 5

Taurultam Solution

One preferred solution comprises:

| | |
|---|---|
| Lactobionic acid | 35.830 g |
| Adenosine | 1.340 g |
| Raffinose Pentahydrate | 17.830 g |
| Hydroxyethyl starch (HES) PL 40/0.5 | 50.000 g |
| Glutathione | 0.929 g |
| Allopurinol | 0.136 g |
| Taurultam | 10.000 g |
| Kcl | 5.200 g |
| MgS0$_4$ 7H$_2$O | 1.230 g |
| NaOH 25% GV to pH 7.8 | |
| NaOH pellets Merck 6482 | |
| Distilled water | 900 ml |

The solution was sterilized from 16 minutes at 121C C. The pH after sterilization was 7.2, and pH of ready to use solution was 7.47.

EXAMPLE 6

Three-cycle treatment Schedule for Treating Patients with Mesothelioma Using a Taurolidine 2% Solution One bottle (250 ml) of 2% taurolidine solution is administered daily via a catheter in the pleural cavity to a patient with mesothelioma, together with four bottles (250 ml each) of 2% taurolidine solution administered intravenously to said patient, at a rate of 40 drops per minute, one bottle every six hours. The dosing cycle consists of an administration phase of daily infusions for five days, followed by a non-administration phase of two days. This dosing cycle is repeated two times (three one week dosing cycles) followed by a three week observation cycle to complete one treatment cycle. This six week treatment cycle is repeated two more times for a total of three treatment cycles.

EXAMPLE 7

Treatment of Mesothelioma in Human Patients

Human patients which may be treated can be male or female, 18 years of age or older, with histological confirmation of a diagnosis of malignant mesothelioma for which there are no standard therapeutic options available. This criteria is encountered when the stage of the disease is III/IV (IMIG classification) or in those patients with progressive disease after a first line therapy with surgery and/or chemotherapy. Patients with first diagnosis of MM and older than 70 or 75 years of agent, who satisfy the other eligibility criteria of such protocol, may receive taurolidine intrapleurally and/or intravenously.

Each patient undergoes a medical evaluation and it will be established by review of the patients's medical records that the patient has malignant mesothelioma of pleural origin (must have histological confirmation) for which there are no standard therapeutic options available.

Each patient has a pleural catheter placed between the 2nd and the 6th if the pleural space is accessible.

Three weeks of treatment followed by three weeks of observation constitute one cycle of treatment.

3 cycles:
Intrapleural: 5 days daily 1×250 ml Taurolin® 2% Taurolidine
Intravenous: 5 days daily 4×250 ml Taurolin® 2% Taurolidine After each three-week taurolidine treatment period, patients are observed for three weeks for safety. Safety is assessed in all patients by the measurements of vital signs, physical examinations, clinical laboratory evaluations, adverse events, 12-load electrocardiograms, and chest x-rays. Patients maybe treated for an additional cycle with taurolidine at the same dose level if desired.

Preliminary anti-tumor activity is assessed at the end of treatment Cycle II by thoracoscopy, thoracic CT and PET scan, Interleukin-6 (IL-6) level in pleural fluid, pulmonary function testing, and performance status. If there is either regression or no progression of the tumor, the patient may be treated for additional six-week cycle(s).

Only some of patients with mesothelioma cannot be treated by intrapleural instillation because there is no intracostal room between the lung tissue and chest wall. It must be checked by computer-tomography whether it is possible to insert a thoracic catheter for intrapleural instillation. Alternatively there might be an intercostal space after surgery (auxiliary intercostal space).

EXAMPLE 8

Therapy of Mesothelioma with Taurolidine

The following is a case involving treatment of an individual for two treatment cycles.
Patient Characteristics:
Patient: Male 44 yrs. old
Diagnosis: Malignant mesothelioma two yrs. ago (stage III according to IMIG stadiation)
Prior treatments: Treated with CT with Cis-Platinum/Gemcitabine, Local recurrency with pleural effusion.

Treatment Characteristics:
Treated with taurolidine 2%, Two cycles of three weeks with taurolidine both intravenous and intrapleural administration
I.V: 4 bottles daily for 5 days for three weeks (2 cycles)
I.P: 1 bottle daily for 5 days for three weeks (2 cycles)
Main Side Effects:
I.V: Mild local burning at the site of instillation, Transient symptomatic hypthension,
I.P: Local burning at the site of instillation, Thoracic burning of significant grade.
None of the above described side effects obliged discontinuance of the treatment.
Preliminary Response Evaluation:
Clinical: Highly significant reduction of the dyspnea,
CT response: CR according to RECIST criteria.
This treatment surprisingly and unexpectedly resulted in a marked improvement of the patient's condition.

I claim:

1. A method of treating mesothelioma in a mammal suffering from mesothelioma, comprising administering to said mammal a mesothelioma tumor cell- inhibiting amount of a tumor-inhibiting methylol-containing compound, wherein the methylol-containing compound is administered intrapleurally and intravenously simultaneously to said mammal, wherein the methylol-containing compound is selected from taurolidine, taurultam, or a mixture thereof.

2. The method of claim 1, wherein said intrapleural administration is direct administration into a mammal's pleural cavity by catheter.

3. The method of claim 1, wherein said intravenous administration is infusion of a solution containing the methylol-containing compound to said mammal intravenously.

4. The method of claim 3, wherein the methylol-containing is administered in one or more treatment cycles, each treatment cycle comprising one or more dosing cycles and one or more observation cycles, during which observation cycle said methylol-containing compound is not administered to the mammal, and wherein each dosing cycle includes an administration phase of one or more days and up to about 8 days during which administration phase said methylol-containing compound is administered each day, at a total daily dosage of about 2 g to 60 g of said methylol-containing compound, each dosing cycle further includes a non-administration phase from about 1 day to about 14 days, during which said methylol-containing compound is not administered to the mammal.

5. The method of claim 4 wherein the non-administration phase is about 1 to 14 days, and 3 or more said dosing cycles are utilized.

6. The method of claim 3, wherein said intravenous administration comprises infusion of a daily dosage of methylol-containing compound as a series of partial doses, each partial dose infusion followed by a break during which no infusion occurs.

7. The method of claim 6, wherein each partial dose is infused over a course of two hours, followed by a break of four hours.

8. The method of claim 7, wherein each daily infusion comprises four 250 ml dose portions of 2% taurolidine by weight, each dosage portion infused over the course of about one to two hours, followed by a non-administration break of about one to six hours.

9. The method of claim 3, wherein an electrolyte solution is co-administered with said solution containing the methylol-containing compound.

10. The method of claim 1, wherein the methylol-containing compound is taurolidine.

11. The method of claim 10, wherein the taurolidine is administered in a daily dose of about 2 g to about 30 g.

12. The method of claim 1, wherein the methylol-containing compound agent is taurultam.

13. The method of claim 12, wherein the taurultam is administered in a daily dose of about 4 g to about 60 g.

14. The method of claim 1, wherein the methylol-containing compound is administered in a dosage of about 150 to 450 mg/kg body weight per day.

15. The method of claim 14, wherein the methylol-containing compound is administered in a dosage of about 300 to 450 mg/kg body weight per day.

16. The method of claim 1, wherein said mesothelioma is pleural mesothelioma.

17. The method of claim 1, wherein the methylol-containing compound comprises taurolidine.

18. The method of claim 1, wherein the methylol-containing compound comprises taurultam.

19. A method of treating mesothelioma in a mammal suffering from mesothelioma, comprising administering to said mammal a mesothelioma tumor cell-inhibiting amount of a compound selected from the group consisting of taurolidine, taurultam and a mixture thereof, wherein said administering is both intrapleural and intravenous.

20. The method of claim 19, wherein said compound is administered in an amount effective to reduce dyspnea in said mammal.

* * * * *